United States Patent [19]
Flynn

[11] Patent Number: 5,085,649
[45] Date of Patent: Feb. 4, 1992

[54] TORQUE CONTROLLED TUBING

[76] Inventor: Vincent J. Flynn, 130 New Rd.-D10, Parsippany, N.J. 07054

[21] Appl. No.: 616,798

[22] Filed: Nov. 21, 1990

[51] Int. Cl.$^5$ ............................................ A61M 25/00
[52] U.S. Cl. .................................... 604/282; 604/264; 128/658
[58] Field of Search .................. 604/280, 282, 96, 264, 604/265, 266, 270; 128/658

[56] References Cited

U.S. PATENT DOCUMENTS

| | | | |
|---|---|---|---|
| 3,618,614 | 11/1971 | Flynn | 604/282 |
| 4,282,876 | 8/1981 | Flynn | 128/658 |
| 4,385,635 | 5/1983 | Ruiz | 128/658 |
| 4,425,919 | 1/1984 | Alston | 604/282 |
| 4,627,844 | 12/1986 | Schmitt | 604/280 |

Primary Examiner—Francis Jaworski
Assistant Examiner—Scott R. Akers
Attorney, Agent, or Firm—Sheldon H. Parker

[57] ABSTRACT

Catheter tubing suitable for medical uses is disclosed, comprising an interior tubular portion and a concentric outer shell, wherein said interior portion extends beyond said concentric outer shell on at least one end of the longitudinal axis, and wherein the hardness of the concentric outer shell exceeds the hardness of the interior tubular portion, the interior tubular portion further comprising at least two resins co-tapered with respect to each other, the hardness of the innermost of which exceeds the hardness of the outermost.

11 Claims, 1 Drawing Sheet

TORQUE CONTROLLED TUBING

The present invention relates to new improved catheter tubing suitable for medical uses. More particularly, it relates to catheter tubing comprising an interior tubular portion and a concentric outer shell, wherein said interior tubular portion comprises at least two cotapered resins and extends beyond said concentric outer shell on at least one end of the longitudinal axis, and wherein the hardness of the innermost of the two cotapered resins exceeds the hardness of the outermost resin and the hardness of the concentric outer shell resin exceeds the hardness of the outermost resin of the cotapered interior tubular portion.

BACKGROUND OF THE INVENTION

Ruiz, U.S. Pat. No. 4,385,635, discloses an angiographic catheter having a soft flexible, pliable, leading tip zone, wherein the catheter is composed of a main reinforced length and an intermediate zone between the tip zone and the main length, the main length being reinforced by an inner tube of a polyamide material and wherein the polyamide is tapered in the intermediate zone to provide a tapered reinforced section tapering distally and uniformly to zero of the tip zone, so that the distal end is of elastomeric material, such as urethane, constituting a soft tip. Flynn, U.S. Pat. No. 4,282,876, discloses multiwall and co-tapered multiwall tubing constructions, wherein either the interior tubular portion or the concentric outer shell comprises a radiopaque composition. Burlis et al., U.S. Pat. No. 3,752,617, relates to the extrusion of tubing having different characteristics along its axial length. Flynn, U.S. Pat. No. 3,618,614, discloses multiwall surgical tubing comprising a relatively thick, transparent tube encased in a relatively thin, visually transparent outer shell. In a preferred embodiment, the thermoplastic material of said outer shell will be a denser, stiffer material than that of the core material to provide adequate torque resistance to the assembly and to provide the hard, slick exterior properties desired.

The prior art illustrates attempts to provide flexible catheter tubing with a soft tip and a stiff body, in order to provide the required degree of insertion and manipulation ease without producing patient trauma in the sensitive internal passageways. Rigidity is required to allow advancement of the catheter by pushing, to allow susceptibility to axial movements of adjustment and to resist twisting or torque forces. Such catheters must also be able to withstand a high bursting pressure.

For example, in constructing tubing for use in artificial kidney connections to the patient, it is desirable to have a tube with a stiff end and a flexible end. One method of constructing such tubing in the past has been to chemically remove the plasticizer from one end of the tube. Another method of making such a tube is to take two separate sections of different plastic tubes and fasten them together employing a suitable joining process. Neither of these methods have been completely satisfactory. The chemical removal of plasticizer results in inconsistent levels of flexibility in the end of the tube, and fastened tube sections possess the inherent risk of separation, causing internal injuries to the patient.

As shown above, some catheter tubing constructions found in the art have also attempted to increase resistance to torque by co-tapering different resins. While such a method may have the effect of providing enhanced torque resistance on one end of the tube, the torque resistance diminishes as the co-tapering progresses. As a result, co-tapering as a method to increase torque resistance, when used alone, is not sufficient to provide torque resistance throughout the entire non-tip length of the tubing. Thus, such tubing is not adequate for complicated applications where high torque resistance is required throughout the length of the tubing to provide ease of application through tortuous body passages.

The catheter tubing constructions found in the art also do not provide the combination of torque resistance and a soft tip, because the soft tip has generally inconsistent properties and is a solid, non-connected part of the tubing. For instance, neither Flynn, U.S. Pat. No. 4,282,876, nor Flynn, U.S. Pat. No. 3,618,614, provide a soft tip for the tubing.

Surprisingly, catheter tubing comprising a hard outer shell and a soft interior portion provides the resistance to torque required for insertion through tortuous body passages, without diminished flexibility or diminished frictional effect. Furthermore, such constructions, by utilizing soft interior portions, are more responsive to guide wire control than are hard interior portions. Additionally, constructions in which the soft interior portion extends beyond the hard outer shell obviates the need for attaching a soft tip to the tubing, thus avoiding the risk of separation of element. This is precisely the opposite approach than was taken by Ruiz, who emphasizes the desirability of having a soft outer shell.

BRIEF DESCRIPTION OF THE DRAWINGS

The present invention will be better understood by reference to the accompanying drawing in which is shown an enlarged, fragmentary cross-sectional view along the longitudinal axis of a typical tube of this invention having a co-tapered interior tubular portion comprising an innermost resin (2) and an outermost resin (4) and a concentric outer shell, wherein said interior portion extends beyond the concentric outer shell on one end of the longitudinal axis, and wherein the hardness of the innermost resin (2) and that of the concentric outer shell resin exceeds the hardness of the outermost resin (4) of the tubular interior portion.

SUMMARY OF THE INVENTION

Figure 1:
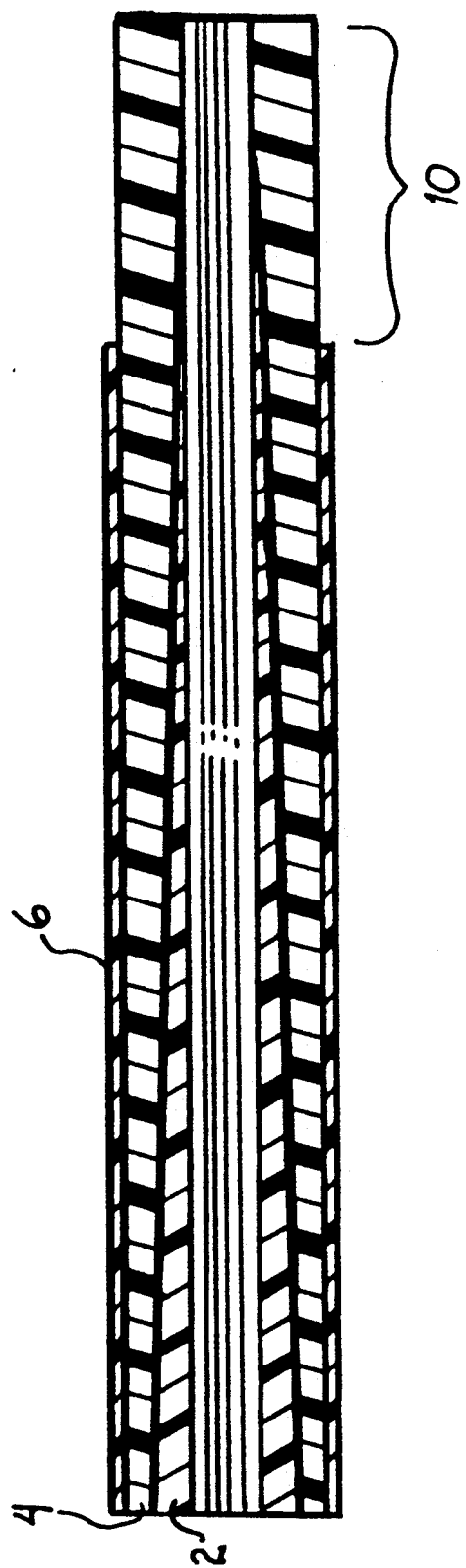

In accordance with the present invention there is provided catheter tubing suitable for medical uses, comprising an interior tubular portion and a concentric outer shell, wherein the interior portion extends beyond the concentric outer shell on at least one end of the longitudinal axis, and wherein the interior tubular portion comprises a first innermost resin (2) and a second outermost resin (4), the tubing having a first point along its length and a second point along its length spaced apart from said first point, the thickness of the first resin (2) tapering as it passes from the first point to the second point and the thickness of second resin (4) tapering inversely to the taper of the first resin (2) as it passes from the first point to the second point, and wherein the hardness of the innermost resin (2) exceeds the hardness of the outermost resin (4) in the interior tubular portion and the hardness of the concentric outer shell resin exceeds the hardness of the second resin (4).

Preferred features of the invention comprise catheter tubing as defined above wherein the interior tubular portion extends beyond the shell by at least about 1.0 inches, and especially such tubing wherein the interior tubular portion extends beyond the shell by from about 1.0 to about 20.0 inches. Also preferred is catheter tubing as defined above wherein the first innermost resin (2) comprises a resin having a Shore D hardness in the range of about 45 to about 80, and wherein the second outermost resin (4) comprises a resin having a Shore A hardness in the range of about 40 to about 100, special mention being made of catheter tubing wherein the concentric outer shell comprises a resin having a Shore D hardness in the range of about 45 to about 85.

Also contemplated by the invention is catheter tubing as defined above wherein the interior tubular portion and the concentric outer shell are essentially of uniform diameter throughout the length of the tubing, excluding the extension of the interior tubular portion and wherein the inner shell has an outer diameter of from about 0.030 to about 0.072 inches and the outer shell has a wall thickness of from about 0.002 to about 0.010 inches.

Among the embodiments of the invention are catheter tubings as defined above wherein the first innermost resin (2) comprises a resin selected from nylon, high density polyethylene, polypropylene, or a mixture of any of them; the second outermost resin (4) comprises a resin selected from polyurethane, an extrudable polyvinyl chloride, and medium density polyethylene or a mixture of any of them; and the concentric outer shell comprises a resin selected from a fluoropolymer, high density polyethylene, ultra high density polyethylene, polycarbonate, nylon or a mixture of any of them; and special mention is made of such tubing wherein the first innermost resin (2) comprises nylon, the second outermost resin (4) comprises polyurethane, and the concentric outer shell comprises high density polyethylene.

The invention further contemplates providing catheter tubings as above defined wherein the second outermost resin (4) further comprises an effective amount of a radiopacifier comprising an ester of a polyiodobenzoic acid, special mention being made of such catheter tubing wherein the ester comprises butyl 2,3,4,6- tetraiodobenzoate.

In a further major aspect the invention provides catheters formed by heat shaping the tubing defined above.

DETAILED DESCRIPTION OF THE INVENTION

Polyurethanes are known to those skilled in the art. They are described in the Modern Plastics Encyclopedia, 1989 Edition, McGraw Hill, New York, pages 136-138. They are also commercially available from a number of suppliers, such as Dow Chemical as Pellethane 2363 Series 80 A-65 D and 75D (therein and herein, A and D designates Shore Hardness, a well known measurement to those skilled in the art of plastic resin formulation: A Series being lower hardness than D Series and the numerical values within each Series increasing with hardness) and "ISOPLAST" RTPU Resins, and also products from B. F. Goodrich Co. tradenamed ESTANE Resins and from Thermedics Co. tradenamed "Tecoflex" Resins.

Polyvinyl chloride is described in the Modern Plastics Encyclopedia, Id., pages 118-127. It is also commercially available from a number of suppliers, such as B. F. Goodrich tradenames GEON 3400 and 3500 Series, as well as Borden Co. and Union Carbide Co. Medium density polyethylene is described in the Modern Plastics Encyclopedia, Id., pages 63-74. It is also commercially available from a number of suppliers, such as U.S.I. Chemicals Co., Dow Chemical Co., Chevron Co., and DuPont Co.

High density polyethylene is described in the Modern Plastics Encyclopedia, Id., pages 63-74. It is also available from a number of suppliers, such as U.S.I. Chemicals Co., Chevron Co., and DuPont Co..

Ultra high density polyethylene is described in the Modern Plastics Encyclopedia, Id., pages 63-74. It is also commercially available from a number of suppliers, such as Himont U.S.A., and Celanese-Hoechst Co.

Nylon is described in the Modern Plastics Encyclopedia, Id., pages 30-31. It is also commercially available from a number of suppliers, such as DuPont Co., Monsanto Co. and BASF Co.

Fluoroplastics are described in the Modern Plastics Encyclopedia, Id., pages 24-26. They are also commercially available from a number of suppliers, such as Dupont Co., tradenamed "Teflon" PTFE Resins, and from the Celanese-Hoechst Co.

Polycarbonate is described in the Modern Plastics Encyclopedia, Id., pages 38-41. It is also commercially available from a number of suppliers, such as General Electric Company, tradenamed "Lexan" Resins and from Mobay Corp., tradenamed "Makrolon" Resins.

Butyl tetraiodobenzoates are described in Flynn, U.S. Pat. No. 4,282,876, and references incorporated therein.

The formulations will be aided in some cases by the inclusion of lubricants such as metallic stearate, stearic acid, paraffin wax, mineral oil, etc. in conventional amounts. See U.S. Pat. No. 3,645,955, incorporated herein to minimize an unnecessarily detailed description.

The compositions are prepared and converted into useful products by techniques well known to those skilled in the art.

In one manner of proceeding, the fluid ingredients, e.g. esters of iodobenzoic acid, are blended with the powdered solids, e.g., polyurethane resin, nylon resin, and the like, and, optionally, stabilizers and plasticizers, and then fused and mixed under pressure, e.g. in a Banbury-type mixer, and discharged. Conventional 2-roll compounding techniques can also be used. The composition is cooled and granulated.

If extrusions are to be made, the granulated composition can be fed to a conventional machine, for example, one or more one-inch Killion-type single screw extruders fitted to a bi-orifice extrusion head of a type shown in FIG. 6 of U.S. Pat. No. 4,282,876, and operated at a suitable temperature, e.g., 300 degrees Fahrenheit, and the tubing is formed at a suitable rate, e.g, 7,000-10,000 feet per hour and cut automatically to length.

Referring to the accompanying drawing, the thermoplastic composition for the innermost resin layer 2 of the interior tubular portion is discharged from the inner annular orifice of the bi-orifice extrusion head (not shown) by a first extruder at a decreasing uniform rate. The outermost resin layer 4 is discharged from the concentric outer annular orifice of the extruder head (also not shown), the thermoplastic composition therefor being supplied by a second extruder at an increasing rate inversely proportional to the declining rate of the first extruder. This provides an inner tubular portion with innermost resin layer 2 tapering downward in thickness while the outermost resin layer 4 is tapering upward in thickness. Air pressure provides support for the thermoplastic walls and assists in defining lumen 8 during extrusion. The increasing and decreasing rates of extrusion for innermost and outermost resin layers 2 and 4 may be provided over any convenient length of time cycle to provide continuous lengths of the co-tapered inner tubular portion. The concentric outer shell 6 is comprised of a resin having a Shore D hardness in the range of about 45 to about 85. The hardness of the concentric outer shell 6 must exceed the hardness of the outermost resin layer 4 for optimum results. The concentric outer shell 6 can be put in place in any convenient manner, e.g., such as by slipping on a tube of heat shrinkable thermoplastic material and then heating to shrink it in place, or by providing a heated film coating die of an entirely conventional type immediately downstream of the bi-orifice die in which the cotapered inner tubular portion is formed.

The end of the tubing where the innermost and outermost resin layers extend beyond the outer shell to form the soft tip 10 can be formed by techniques known to those skilled in the art. In one manner of proceeding, the end is centerless ground to remove the concentric outer shell 6, thus exposing the innermost and outermost resin layers 2 and 4 to form the soft tip 10. Other methods can also be used, such as using the aforementioned film coating die and terminating extrusion of the concentric outer shell 6 at any desired length short of the end to produce soft tip 10.

The tubing of this invention can be used for many various and diverse purposes, e.g., heart catheters, stomach tubes, nasal tubes, thoracic catheters, and other catheter tubings suitable for medical uses. However, from the foregoing description and the following examples and by reference to other well known teachings, the methods and modes by which the tubing of this invention can be formed into various other articles will be readily apparent to those skilled in the art.

The medical grade tubing prepared as described in the following examples will be non-toxic, non-reactive to tissue and may be sterilized by gas or cold sterilization solutions. The tubing is generally dispensed as such and the surgeon or trained technician will form it into catheters for roentgenography. For maximum convenience, the tubing can also be preformed into articles and dispensed, e.g., as sterile disposable intravenous catheters.

By way of illustration, catheters according to this invention will be fabricated from the medical-surgical tubing of the invention by operations comprising tip forming, tip finishing, shaping, side hole forming, and flaring. Before use they will be sterilized.

Those skilled in the art will prepare a variety of tip shapes. For internal mammary and axillary artery branches a three-quarter loop is formed in the distal end. For percutaneous arteriography and cerebral arteriography via femoral, a 45–60 degree smooth bend will be formed in the distal end. Selective renal arteriography and celiac arteriography requires a one-half loop. Hepatic venography uses about a seven-eighths loop. For trans-septal left-heart catheterization via the femoral vein, a three-quarter loop, like that above-described for mammary branches, but larger, is formed. On the other hand, abdominal aortography via brachial artery uses a rather large, one-third closed loop and thoracic aortography via the femoral artery uses the same shape but bigger. For lumbar aortography via the femoral artery the tip is straight out. For coronary arteriography, the end of the catheter is looped.

The heavier-walled tubing is formed into such typical shapes by inserting a forming wire within the tubing and heating in a tiny flame until visibly softened. By pulling from both ends the tubing is drawn to the wire and forms a uniform lumen around it. The tip is formed by cutting, e.g., with a razor blade, at the drawn diameter and is smoothly rounded in the flame. Next a precurved wire is inserted into the tube which is then immersed in hot water until the tubing softens. Quenching in cold water will cause the catheter to conform to the curve of the forming wire. Side hole or eye punching is accomplished by rotating a sharpened hole punch cannula under slight pressure. The holes should be large enough to expel contrast media without excess build up of injection pressures but should be no larger than 2/3 of the internal diameter of the tubing. The catheter is cut to the preselected length and flared. Heating in a small flame and rotating on a flaring tool produces a flare of the desired size. The catheter can be bonded at the flare, e.g., with epoxy cement, to a suitable hub. On the other hand, an adapter can be used to screw the catheter to a Luer-Lok stopcock, or the like.

DESCRIPTION OF THE PREFERRED EMBODIMENTS

The following examples illustrate the present invention but are not intended to limit the claims in any manner whatsoever.

Example 1

A co-tapered multiwall tube in made and covered with a heat shrunk outer shell. The innermost and outermost layers are extruded concurrently and concentrically through annular concentric orifices of a multiorifice extruder so as to bond the inner and outer layers together. The co-tapering of the inner and outer layers is obtained by varying the rate of extrusion of the inner and outer layer. See the above-mentioned Burlis et al patent and Flynn, U.S. Pat. No. 4,282,876. The rate of extrusion of the inner layer gradually varies from a first rate to a second rate while the rate of extrusion of the outer layer gradually varies inversely for the inner layer. The inner layer comprises nylon having a hardness in the range of Shore D 46–78. The outermost layer comprises polyurethane having a hardness in the range of Shore A 55–95. Next a sleeve of heat shrinkable fluoroplastic (polytetrafluoroethylene having a hardness in the range of Shore D 50–65) is slipped over the cotapered tubing and the multiwall tubing is heated to shrink the outer tube and form a shell. Finally a portion of the shell is removed by centerless grinding from one end of the tube to leave a two inch end comprising the exposed interior tubular portion as shown in the drawing.

The outside diameter of the inner tubular portion is about 0.050 inches and the wall thickness of the outer shell is about 0.004 inches.

Surgical catheters are formed from lengths of the tubing, for example 40-inch lengths, and they exhibit a degree of flexability and softening progressively changing from one end to the other. Such medical surgical catheters have manipulative characteristics which are advantageously employed by the surgical operator in inserting, withdrawing and controlling the catheter.

EXAMPLE 2

The procedure of Example 1 is repeated except that the outermost layer of the inner tubular portion is substituted with a 55 to 65 Shore D hardness thermoplastic polyurethane containing 20 parts per 100 parts by weight of composition of n-butyl 2,3,4,6-tetraiodobenzoate. Medical surgical tubing according to this invention is obtained which, in addition to posessing the manipulative advantages described above, is highly radiopaque and has advantageously improved tensile properties over known radiopacified multiwall radiopacified tubing.

The above-mentioned patents, publications and test methods are incorporated herein by reference.

The foregoing detailed description will suggest many obvious variations to those skilled in the art. For example, instead of butyl tetraiodobenzoate, a mixture thereof with an ester of 2,5-diodobenzoic acid can be used. Instead of polyurethane, a flexible poly(vinyl chloride) resin can be used in the outermost layer of the inner tubular portion. Instead of poly(tetrafluoroethylene) in the shell, there can be used high density polyethylene, ultra high density polyethylene, polycarbonate resin, or high hardness nylon. Instead of nylon in the innermost layer of the interior tubular portion, there can be used high density polyethylene, or polypropylene. Any of the layers can also comprise mixed such resins. All such obvious modifications are within the full intended scope of the appended claims.

I claim:

1. Catheter tubing suitable for medical uses, comprising an interior tubular portion and a concentric outer shell, wherein said interior portion extends beyond said concentric outer shell on at least one end of the longitudinal axis, and wherein said interior portion comprises a first innermost resin (2), and a second outermost resin (4), said tubing having a first point along its length and a second point at or beyond said concentric outer shell (6) along its length spaced apart from said first point, the thickness of said first resin (2) tapering in a decreasing fashion as it passes from said first point to said second point an the thickness of said second resin (4) tapering inversely to the taper of said first resin (2) as it passes from said first point to said second point, and wherein the hardness of the innermost resin (2) exceeds the hardness of the outermost resin (4) in the interior tubular portion and the hardness of the concentric outer shell exceeds the hardness of said second resin (4).

2. Catheter tubing as defined on claim 1 wherein said interior tubular portion extends beyond said shell by at least about 1.0 inches.

3. Catheter tubing as defined in claim 2 wherein said interior tubular portion extends beyond said shell by from about 1.0 to about 20.0 inches.

4. Catheter tubing as defined in claim 1, wherein said first innermost resin (2) comprises a resin having a Shore D hardness in the range of about 45 to about 80, and wherein said second outermost resin (4) comprises a resin having a Shore A hardness in the range of about 40 to about 100.

5. Catheter tubing as defined in claim 4, wherein said concentric outer shell comprises a resin having a Shore D hardness in the range of about 45 to about 85.

6. Catheter tubing as defined in claim 1, wherein the interior tubular portion and the concentric outer shell are essentially of uniform diameter throughout the length of the tubing, excluding the extension of said interior tubular portion and wherein said inner shell has an outer diameter of from about 0.030 to about 0.072 inches and said outer shell has a wall thickness of from about 0.002 to about 0.010 inches.

7. Catheter tubing as defined in claim 1, wherein said first innermost resin (2) comprises a resin selected from the group consisting of nylon, high density polyethylene, polypropylene, or a mixture of any of them; said second outermost resin (4) comprises a resin selected from the group consisting of polyurethane, an extrudable polyvinyl chloride, and a medium density polyethylene and a mixture thereof; and said concentric shell comprises a resin selected from a fluoropolymer, high density polyethylene, ultra high density polyethylene, polycarbonate, nylon and a mixture thereof.

8. Catheter tubing as defined in claim 7, wherein said first innermost resin (2) comprises nylon, said second outermost resin (4) comprises polyurethane, and said concentric outer shell comprises high density polyethylene.

9. Catheter tubing as defined in claim 1 wherein said second outermost resin (4) further comprises an effective amount of a radiopacifier comprising an ester of a polyiodobenzoic acid.

10. Catheter tubing as defined in claim 9, wherein said ester comprises butyl 2,3,4,6-tetraiodobenzoate.

11. A catheter, said catheter being produced by the process of heat shaping the catheter tubing defined in claim 1.

* * * * *